(12) United States Patent
Okuno et al.

(10) Patent No.: US 9,700,277 B2
(45) Date of Patent: Jul. 11, 2017

(54) X-RAY APPARATUS

(71) Applicant: SHIMADZU CORPORATION, Kyoto-shi, Kyoto (JP)

(72) Inventors: Tomoharu Okuno, Kyoto (JP); Takashi Marume, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 10 days.

(21) Appl. No.: 14/432,894

(22) PCT Filed: Sep. 17, 2013

(86) PCT No.: PCT/JP2013/075045
§ 371 (c)(1),
(2) Date: Apr. 1, 2015

(87) PCT Pub. No.: WO2014/054417
PCT Pub. Date: Apr. 10, 2014

(65) Prior Publication Data
US 2015/0250441 A1 Sep. 10, 2015

(30) Foreign Application Priority Data
Oct. 2, 2012 (JP) ................................. 2012-220433

(51) Int. Cl.
*A61B 6/00* (2006.01)
*A61B 6/06* (2006.01)

(52) U.S. Cl.
CPC ................ *A61B 6/547* (2013.01); *A61B 6/06* (2013.01); *A61B 6/5205* (2013.01); *A61B 6/5241* (2013.01); *A61B 6/4452* (2013.01)

(58) Field of Classification Search
CPC ....... A61B 6/06; A61B 6/4452; A61B 6/5205; A61B 6/5241; A61B 6/547
See application file for complete search history.

(56) References Cited

U.S. PATENT DOCUMENTS 9,155,507 B2 * 10/2015 Behiels ................ A61B 6/5229
9,265,467 B2 * 2/2016 Kamiya ............... A61B 6/5241
(Continued)

FOREIGN PATENT DOCUMENTS

| CN | 102138803 A | 8/2011 |
|----|-------------|--------|
| CN | 102316806 A | 1/2012 |

(Continued)

OTHER PUBLICATIONS

English translation, International Search Report PCT/JP2013/075045 dated Dec. 3, 2013.
(Continued)

*Primary Examiner* — Wyatt Stoffa
(74) *Attorney, Agent, or Firm* — McDermott Will & Emery LLP

(57) ABSTRACT

In an X-ray apparatus in which an FPD-4 moves independently of an X-ray tube, an X-ray irradiation area discriminator discriminates, for separate X-raying actions, X-ray irradiation area images from among X-ray images outputted from the FPD-4. An X-ray tube position sensor acquires position information P on the X-ray tube for the separate X-raying actions. A long image creator creates a long image by shifting the X-ray irradiation area images based on the position information, and splicing the X-ray irradiation area images together. Therefore, even when a relative position between the X-ray tube and FPD-4 is variable instead of being constant, the X-ray irradiation area images can be obtained reliably, and these can be spliced together with high accuracy. There is no need to uniform starting timing and moving speed of the X-ray tube and FPD-4, which simplifies control.

6 Claims, 9 Drawing Sheets

(56) References Cited

U.S. PATENT DOCUMENTS

| | | | | |
|---|---|---|---|---|
| 2008/0152088 | A1* | 6/2008 | Wang | A61B 6/02 378/98.12 |
| 2009/0257561 | A1* | 10/2009 | Okuno | A61B 6/4233 378/116 |
| 2010/0074505 | A1 | 3/2010 | Oogami | |
| 2010/0290592 | A1* | 11/2010 | Yamada | A61B 6/00 378/114 |
| 2011/0038454 | A1* | 2/2011 | Minnigh | A61B 6/06 378/62 |
| 2011/0150179 | A1* | 6/2011 | Kato | A61B 6/4233 378/62 |
| 2011/0206185 | A1* | 8/2011 | Sakai | A61B 6/06 378/62 |
| 2012/0050327 | A1* | 3/2012 | Takekoshi | G06T 3/4038 345/634 |
| 2012/0224672 | A1* | 9/2012 | Yamada | A61B 6/00 378/98 |
| 2012/0288056 | A1* | 11/2012 | Murakoshi | A61B 6/4233 378/37 |
| 2013/0315372 | A1* | 11/2013 | Behiels | A61B 6/06 378/62 |

FOREIGN PATENT DOCUMENTS

| | | |
|---|---|---|
| JP | 2007-267787 A | 10/2007 |
| JP | 2010-75245 A | 4/2010 |
| JP | 2010-227372 A | 10/2010 |
| JP | 2010-240247 A | 10/2010 |
| JP | 2011-50494 A | 3/2011 |
| JP | 2012-50515 A | 3/2012 |
| WO | 2010/050032 A1 | 5/2010 |

OTHER PUBLICATIONS

"Slot Radiography", Shimadzu Corporation, URL http://www.med.shimadzu.co.jp.safire/appli/02.html with partial English translation.
Notification of Reasons for Refusal Japanese Patent Application No. 2014-539658 dated Jun. 28, 2016 with English translation.
Office Action and Search Report issued in Chinese Patent Application No. 201380051885.1, dated Nov. 1, 2016.

* cited by examiner (a)

(b)

(c)

(d)

(e)

X-RAY APPARATUS

RELATED APPLICATIONS

This application is the U.S. National Phase application under 35 U.S.C. §371, of international Application No. PCT/JP2013/075045 filed on Sep. 17, 2013, which in turn claims the benefit of Japanese application No. 2012-220433, filed on Oct. 2, 2012 the disclosures of which Applications are incorporated by reference herein.

TECHNICAL FIELD

This invention relates to an X-ray apparatus for carrying out long-size radiography such as slot radiography which acquires a long image by splicing a plurality of X-ray images.

BACKGROUND ART

Conventionally, an X-ray apparatus includes an X-raying table having a top board for supporting an inspection object M, an X-ray tube for emitting X-rays toward the inspection object (for irradiation), and an X-ray detector disposed opposite the X-ray tube for detecting X-rays transmitted through the inspection object. The X-ray tube is held by an X-ray tube holding device suspended from a ceiling, for example. The X-ray detector is mounted in the X-raying table and in a position opposed to the X-ray tube across the top board.

When X-raying the whole spine or a whole lower limb of the inspection object with this X-ray apparatus, these cannot be fitted at a time in the X-ray detecting area of the X-ray detector. Therefore, a technique called long-size radiography is used (see Patent Documents 1 and 2, for example). Long-length radiography is carried out as follows. First, radiography is carried out while translating the X-ray tube and X-ray detector along the inspection object to obtain a plurality of consecutive X-ray images. Then, one long image is created by splicing together the plurality of X-ray images obtained.

Further, long-size radiography includes a technique called slot radiography which obtains a long image by contracting emitted X-rays to a slit shape (also called a slot shape) (see Patent Document 3 and Nonpatent Document 1, for example). This technique obtains a long image by contracting X-rays to the slit shape, carrying out continuous radiography while translating the X-ray tube and X-ray detector to obtain X-ray images, and splicing together the plurality of X-ray images. The X-rays contracted to the slit shape can be regarded as a parallel X-ray emission from infinity, which can obtain a long image free of distortion. Further, slot radiography can suppress the influence of scattered X-rays, and can therefore obtain a high definition long image.

PRIOR ART DOCUMENTS

Patent Documents

[Patent Document 1]
Unexamined Patent Publication No. 2010-075245
[Patent Document 2]
Unexamined Patent Publication No. 2010-240247
[Patent Document 3]
International Publication 2010/050032

Nonpatent Document

[Nonpatent document 1]
"Slot Radiography", Shimadzu Corporation URL<http://www.med.shimadzu.co.jp/safire/appli/02.html>

SUMMARY OF INVENTION

Technical Problem

However, the conventional X-ray apparatus for carrying out slot radiography has the following problems. With the X-ray apparatus, radiography is carried out in such a mode that an X-ray axis, which is the center of the X-rays emitted from the X-ray tube, is located at the center of a detecting plane which is the X-ray detecting area of the X-ray detector. That is, the X-ray tube and X-ray detector are moved synchronously along the body axis direction of an inspection object so that a relative position of the X-ray tube and the X-ray detector will always be the same. It is therefore necessary to provide drive to uniform starting timing of the X-ray tube and X-ray detector, and moving speed of the X-ray tube and X-ray detector. Particularly where the X-ray tube and X-ray detector are driven independently of each other, it is difficult to uniform the above timing and the moving speed with high accuracy. Further, the X-ray tube and X-ray detector are accelerated so that times taken until they reach a state of constant speed movement be in agreement. Where a flat panel X-ray detector (which will hereinafter be called "FPD" as appropriate) is used as X-ray detector, the FPD is generally heavier than the X-ray tube. When one of them has a later acceleration time than the other, the time taken until radiography will become the longer for the delay thereby caused. Thus, with the conventional apparatus, complicated control must be performed, which requires expensive motors such as AC servomotors. Consequently, the apparatus has inevitably become expensive.

The following problems are disclosed in Patent Document 3. That is, movement of the FPD does not necessarily occur according to setting, but has some displacement from the setting. When a moving distance of the FPD relative to an inspection object is too long, unexpected displacements will occur with fluoroscopic images of the inspection object appearing in slit-shaped images. And since the slit-shaped images are superimposed based on an assumption that the FPD is moving according to the setting, unexpectedly displaced fluoroscopic images are superimposed on one another. So, it is proposed in Patent Document 3 to reduce the unexpected displacements of the fluoroscopic images appearing in the slit-shaped images, by minimizing the moving distance of the FPD relative to the inspection object. However, it is desirable to obtain a long image in which the influence of displacement is suppressed regardless of relative moving distances of the X-ray tube and FPD.

This invention has been made having regard to the state of the art noted above, and its object is to provide an X-ray apparatus which can simplify control of an X-ray tube and an X-ray detector in long-size radiography.

Solution to Problem

To fulfill the above object, this invention provides the following construction.

An X-ray apparatus according to this invention comprises an X-ray source for emitting X-rays toward an inspection object; an X-ray source mover for moving the X-ray source along a body axis of the inspection object; an X-ray detector disposed opposite the X-ray source for detecting X-rays transmitted through the inspection object and outputting them as X-ray images; an X-ray detector mover for moving the X-ray detector along the body axis of the inspection object independently of the X-ray source; a collimator disposed on an X-ray emitting side of the X-ray source to be movable with the X-ray source for contracting emitted X-rays to an area narrower than a detecting area of the X-ray detector in a direction of movement of the X-ray detector; an X-ray irradiation area discriminator for discriminating, for separate X-raying actions, X-ray irradiation area images which are areas of the X-ray images where collimated X-rays are received; a position information acquirer for acquiring position information on the X-ray source for the separate X-raying actions; and a long image creator for creating a long image by shifting the X-ray irradiation area images based on the position information so that a center of each of the X-ray irradiation area images in the direction of movement of the X-ray detector coincide with a position of X-ray incidence at a time of radiography, and by splicing the X-ray irradiation area images together.

According to the X-ray apparatus of this invention, the X-ray source emits X-rays toward the inspection object, and is moved by the X-ray source mover along the body axis of the inspection object. The X-ray detector is provided opposite the X-ray source for detecting X-rays transmitted through the inspection object and outputting them as X-ray images. The X-ray detector mover moves the X-ray detector along the body axis of the inspection object independently of the X-ray source. A collimator is provided on the X-ray emitting side of the X-ray source. The collimator, while contracting emitted X-rays to the area narrower than the detecting area of the X-ray detector in the direction of movement of the X-ray detector, is movable to accompany the X-ray source. The X-ray irradiation area discriminator discriminates, for separate X-raying actions, X-ray irradiation area images which are areas in the X-ray images where collimated X-rays have been received. The position information acquirer acquires position information on the X-ray source for the separate X-raying actions. And the long image creator creates a long image by shifting the X-ray irradiation area images, based on the position information, so that the center of each of the X-ray irradiation area images in the direction of movement of the X-ray detector coincide with a position of X-ray incidence at the time of radiography, and by splicing the X-ray irradiation area images together.

That is, in long-size radiography with the X-ray detector moving independently of the X-ray source, the X-ray irradiation area discriminator discriminates, for separate X-raying actions, X-ray irradiation area images which are areas in the X-ray images having received the collimated X-rays. The position information acquirer acquires position information on the X-ray source for the separate X-raying actions. And the long image creator creates a long image by shifting the X-ray irradiation area images, based on the position information, so that the center of each of the X-ray irradiation area images in the direction of movement of the X-ray detector coincide with a position of X-ray incidence at the time of radiography, and by splicing the X-ray irradiation area images together. Consequently, even when the relative position between the X-ray source and X-ray detector is variable instead of being constant, the X-ray irradiation area images can be obtained reliably, and the X-ray irradiation area images can be spliced to one another with high accuracy. Further, there is no need to uniform starting timing and moving speed of the X-ray source and X-ray detector, which can simplify control and make the apparatus inexpensive.

A conventional X-ray apparatus is controlled such that an X-ray axis of X-rays emitted from the X-ray source is located at the center of the detecting plane which is the X-ray detecting area of the X-ray detector. Therefore, a long-size radiographic range was a distance corresponding to the moving distance of the X-ray detector. However, since this invention allows X-raying to be done in any position on the detecting plane of the X-ray detector, even if the moving distance of the X-ray detector is the same as in the prior art, the long-size radiographic range can be set wide.

An advantage over Patent Document 3 will be described here. According to this invention, the X-ray irradiation area images corresponding to slit-shaped images are discriminated from the X-ray images. The X-ray irradiation area images are areas of irradiating X-rays contracted to the area narrower than the detecting area of the X-ray detector. Therefore, when X-rays are emitted from the X-ray source in a predetermined position, even if the X-ray detector is displaced to a certain extent, the X-ray irradiation area image discriminated and obtained is the same as long as the irradiation X-rays are within the detecting area of the X-ray detector. Therefore, the X-ray irradiation area images discriminated from the X-ray images may be shifted based on the acquired position information on the X-ray source, and then the X-ray irradiation area images may be spliced to one another. In this way, a long image with the influence of displacement suppressed can be obtained regardless of the relative moving distance of the X-ray detector.

In the X-ray apparatus according to this invention, it is preferable that the X-ray detector mover is arranged to move the X-ray detector slower on average than the X-ray source. Being slow on average here means slow when comparison is made in average through a series of operations from start to finish of radiography. Conventionally, a high-output motor is used in order to move the X-ray detector, which is heavier than the X-ray source, similarly to the X-ray source. However, by moving the X-ray detector slower than the X-ray source, it is possible to use a motor having a lower output than in the prior art. Therefore, a power-saving and inexpensive motor can be used, thereby making the apparatus inexpensive.

In the X-ray apparatus according to this invention, one example of the position information acquirer is an X-ray source position sensor. Since actual position information on the X-ray source can be acquired by this, even when errors (displacements) occur, the X-ray irradiation area images can be spliced together with high accuracy.

An advantage over Patent Document 3 will be described here. As noted hereinbefore, when X-rays are emitted from the X-ray source in a predetermined position, even if the X-ray detector is displaced to a certain extent, the X-ray irradiation area image discriminated and obtained is the same as long as the irradiation X-rays are within the detecting area of the X-ray detector. Further, if the position information on the X-ray source used is based on actual positions, the X-ray irradiation area images can be spliced together in a way to allow for displacement of the X-ray source. Therefore, a long image with the influence of displacement suppressed can be obtained regardless of the relative moving distance of the X-ray source and X-ray detector.

In the X-ray apparatus according to this invention, one example of the position information is calculated from radiographing time interval information and X-ray source moving speed information. When the X-raying time interval information and the moving speed of the X-ray source are constant, it becomes unnecessary to provide the X-ray source position sensor, for example. This can simplify the construction, thereby making the apparatus inexpensive.

In the X-ray apparatus according to this invention, the X-ray irradiation area images are images extracted from the X-ray images, for example. Images other than the X-ray irradiation area images can be removed, which can make a data volume smaller than the original X-ray images.

In the X-ray apparatus according to this invention, it is preferable that the X-ray irradiation area discriminator is arranged to add the position information to the X-ray irradiation area images for the separate X-raying actions. This can simplify control of the X-ray irradiation area images and position information. For example, even when a change occurs to the order of the plurality of X-ray irradiation area images for creating a long image, the positions of the X-ray irradiation area images at the time of splicing can be known from the position information added to the X-ray irradiation area images.

In the X-ray apparatus according to this invention, it is preferable that the X-ray source mover is arranged to move the X-ray source at a constant speed. This simplifies control and assures long images of stable quality.

This specification discloses also the invention relating to the following X-ray apparatus.

(1) An X-ray apparatus comprising an X-ray source for emitting X-rays toward an inspection object; an X-ray source angle changer for changing an angle of the X-ray source about an axis set beforehand to extend along a body axis of the inspection object; an X-ray detector disposed opposite the X-ray source for detecting X-rays transmitted through the inspection object and outputting them as X-ray images; an X-ray detector mover for moving the X-ray detector along the body axis of the inspection object independently of the X-ray source; a collimator disposed on an X-ray emitting side of the X-ray source to be movable with the angle of the X-ray source for contracting emitted X-rays to an area narrower than a detecting area of the X-ray detector in a direction of movement of the X-ray detector; an X-ray irradiation area discriminator for discriminating, for separate X-raying actions, X-ray irradiation area images which are areas of the X-ray images where collimated X-rays are received; an angle information acquirer for acquiring angle information on the X-ray source for the separate X-raying actions; and a long image creator for creating a long image by shifting the X-ray irradiation area images based on the angle information so that a center of each of the X-ray irradiation area images in the direction of movement of the X-ray detector coincide with a position of X-ray irradiation at a time of radiography, and by splicing the X-ray irradiation area images together.

The above construction includes an X-ray source angle changer in place of the X-ray source mover described hereinbefore, and an angle information acquirer in place of the position information acquirer. According to the X-ray apparatus having the above construction, in long-size radiography with the X-ray detector moving independently of the X-ray source, the X-ray irradiation area discriminator discriminates, for separate X-raying actions, X-ray irradiation area images which are areas in the X-ray images having received the collimated X-rays. The angle information acquirer acquires angle information on the X-ray source for the separate X-raying actions. And the long image creator creates a long image by shifting the X-ray irradiation area images, based on the angle information, so that the center of each of the X-ray irradiation area images in the direction of movement of X-ray detector coincide with a position of X-ray irradiation at the time of radiography, and by splicing the X-ray irradiation area images together. Consequently, even when the relative position between the X-ray source and X-ray detector is variable instead of being constant, the X-ray irradiation area images can be obtained reliably, and the X-ray irradiation area images can be spliced to one another with high accuracy. Further, there is no need to uniform starting timing and moving speed of the X-ray source and X-ray detector, which simplifies control and makes the apparatus inexpensive.

A conventional X-ray apparatus is controlled such that an X-ray axis of X-rays emitted from the X-ray source is located at the center of the detecting plane which is the X-ray detecting area of the X-ray detector. Therefore, a long-size radiographic range was a distance corresponding to the moving distance of the X-ray detector. However, since this invention allows X-raying to be done in any position on the detecting plane of the X-ray detector, even if the moving distance of the X-ray detector is the same as in the prior art, the long-size radiographic range can be set wide.

Advantageous Effects of Invention

According to the X-ray apparatus of this invention, in long-size radiography with the X-ray detector moving independently of the X-ray source, the X-ray irradiation area discriminator discriminates, for separate X-raying actions, X-ray irradiation area images which are areas in the X-ray images having received the collimated X-rays. The position information acquirer acquires position information on the X-ray source for the separate X-raying actions. And the long image creator creates a long image by shifting the X-ray irradiation area images, based on the position information, so that the center of each of the X-ray irradiation area images in the direction of movement of X-ray detector coincide with a position of X-ray incidence at the time of radiography, and by splicing the X-ray irradiation area images together. Consequently, even when the relative position between the X-ray source and X-ray detector is variable instead of being constant, the X-ray irradiation area images can be obtained reliably, and the X-ray irradiation area images can be spliced to one another with high accuracy. Further, there is no need to uniform starting timing and moving speed of the X-ray source and X-ray detector, which can simplify control and make the apparatus inexpensive.

BRIEF DESCRIPTION OF DRAWINGS

FIG. 3 is a view illustrating a long-size radiographic range, unit radiographic ranges, overlap portions and so on;

DESCRIPTION OF EMBODIMENTS

Embodiment 1

Figure 1:
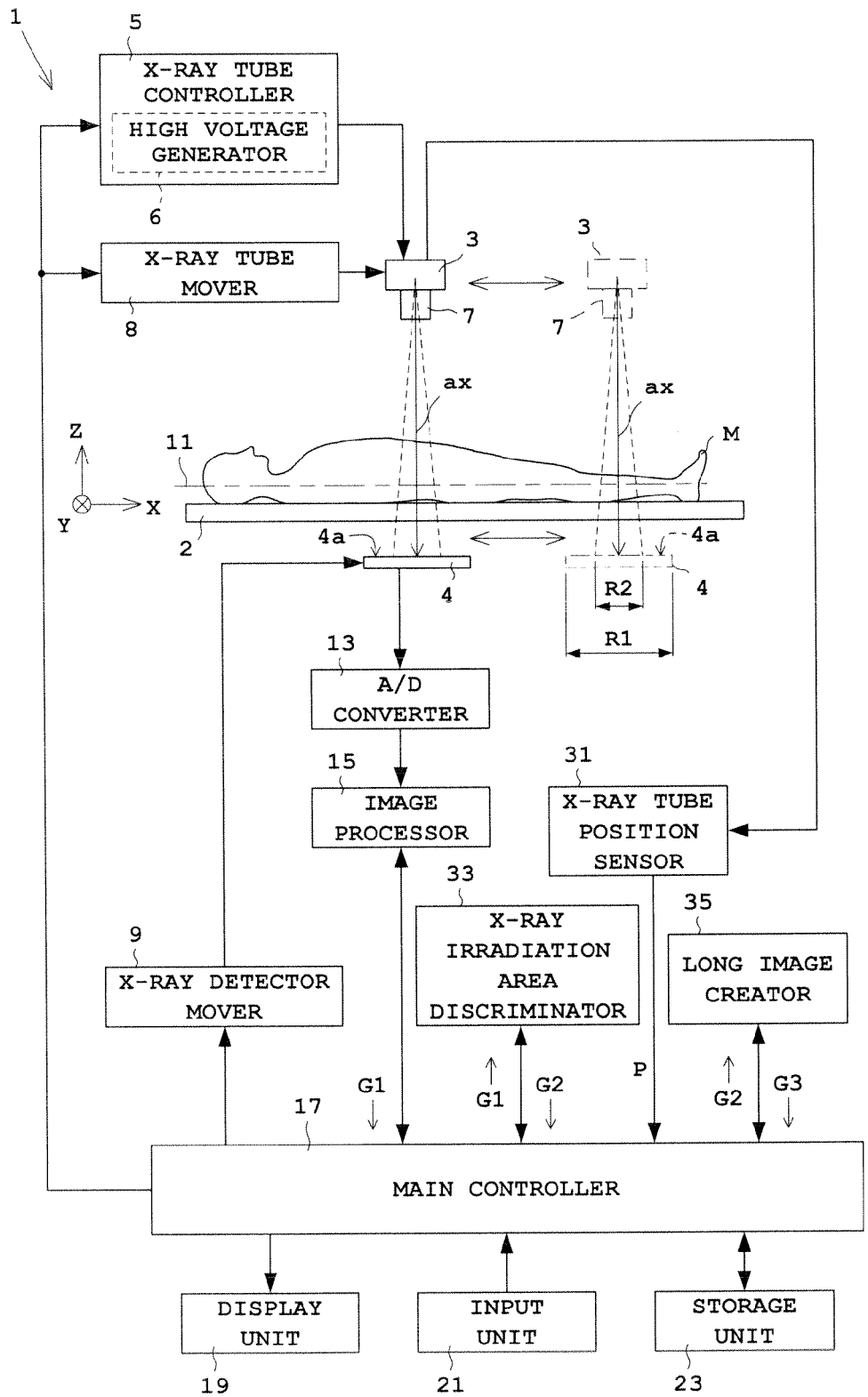
FIG. 1 is a view showing an outline construction of an X-ray apparatus according to Embodiment 1.

Embodiment 1 of this invention will be described hereinafter with reference to the drawings. FIG. 1 is a view showing an outline construction of an X-ray apparatus according to Embodiment 1.

Reference is made to FIG. 1. An X-ray apparatus 1 includes a top board 2 for supporting an inspection object M, an X-ray tube 3 for emitting X-rays toward the inspection object M, and a flat panel X-ray detector (FPD) 4 disposed opposite the X-ray tube 3 for detecting X-rays transmitted through the inspection object M and outputting them as X-ray image. The X-ray tube 3 corresponds to the X-ray source in this invention. The FPD 4 corresponds to the X-ray detector in this invention.

The X-ray tube 3 is controlled by an X-ray tube controller 5. The X-ray tube controller 5 has a high voltage generator 6 for generating a tube voltage and a tube current for the X-ray tube 3. The X-ray tube controller 5 causes the X-ray tube 3 to emit X-rays according to X-ray emitting conditions such as tube voltage, tube current, and irradiation time. The X-ray tube 3 has a collimator 7 provided on an X-ray emitting side thereof for contracting the X-rays emitted from the X-ray tube 3.

The collimator 7 has four leaves (not shown), for example. These four leaves are arranged to shield the X-rays emitted from the X-ray tube 3 and contract the X-rays to irradiate a rectangular area of arbitrary size. The collimator 7 in FIG. 1 is constructed to contract the emitted X-rays, for example, to an area R2 narrower than an detecting area R1 of the FPD 4 in a body axis direction 11 (X-direction) of the inspection object M. The collimator 7 moves to accompany the X-ray tube 3. That is, the collimator 7 is movable with the X-ray tube 3 in an integrated way.

The FPD 4 has numerous X-ray detecting elements arranged in rows and columns of a two-dimensional matrix array on an X-ray detecting plane to which transmitted X-ray images of an object to be detected (inspection object M) are projected, the detecting elements converting the X-rays into electric signals for detection. The matrix array of X-ray detecting elements may, for example, be several thousands×several thousands. The X-ray detecting elements are the direct conversion type for converting X-rays directly into electric signals, or the indirect conversion type for converting X-rays once into light and then further converting it into electric signals.

Further, the X-ray apparatus 1 includes an X-ray tube mover 8 for moving the X-ray tube 3 along the body axis direction 11 of the inspection object M, and an X-ray detector mover 9 for moving the FPD 4 along the body axis direction 11 of the inspection object M independently of the X-ray tube 3. Both the X-ray tube mover 8 and X-ray detector mover 9 move the X-ray tube 3 and FPD 4 along the body axis direction 11 (X-direction) of the inspection object M. That is, the X-ray detector mover 9 moves the FPD 4 parallel to the direction of movement of the X-ray tube 3. The X-ray tube mover 8 moves the X-ray tube 3 at a constant speed, and X-ray radiography is carried out by emitting X-rays from the X-ray tube 3 moved at the constant speed. The X-ray tube mover 8 is formed of an AC servomotor, for example. The X-ray detector mover 9 is formed of a DC brush motor, for example. The X-ray tube mover 8 corresponds to the X-ray source mover in this invention.

Downstream of the FPD 4 there are arranged in order an analog-to-digital converter 13, an image processor 15 and a main controller 17. The analog-to-digital converter 13 converts X-ray images (X-ray detection signals) outputted in analog form from the FPD 4 into X-ray images in digital form. The image processor 15 carries out required processes such as a gradation process on the X-ray images having undergone the digital conversion, and outputs processed X-ray images G1. The main controller 17 performs overall control of the components of the X-ray apparatus 1, and is formed of a central processing unit (CPU) or the like. The main controller 17 controls the X-ray tube mover 8 and X-ray detector mover 9 to move the X-ray tube 3 and FPD 4, for example.

Further, the X-ray apparatus 1 includes a display unit 19, an input unit 21 and a storage unit 23. The display unit 19 is in form of a monitor, for example. The input unit 21 includes a keyboard, a mouse and so on. The storage unit 23 may be storage media including removable media, such as a ROM (Read-only Memory), a RAM (Random-Access Memory) or a hard disk.

Figure 2:
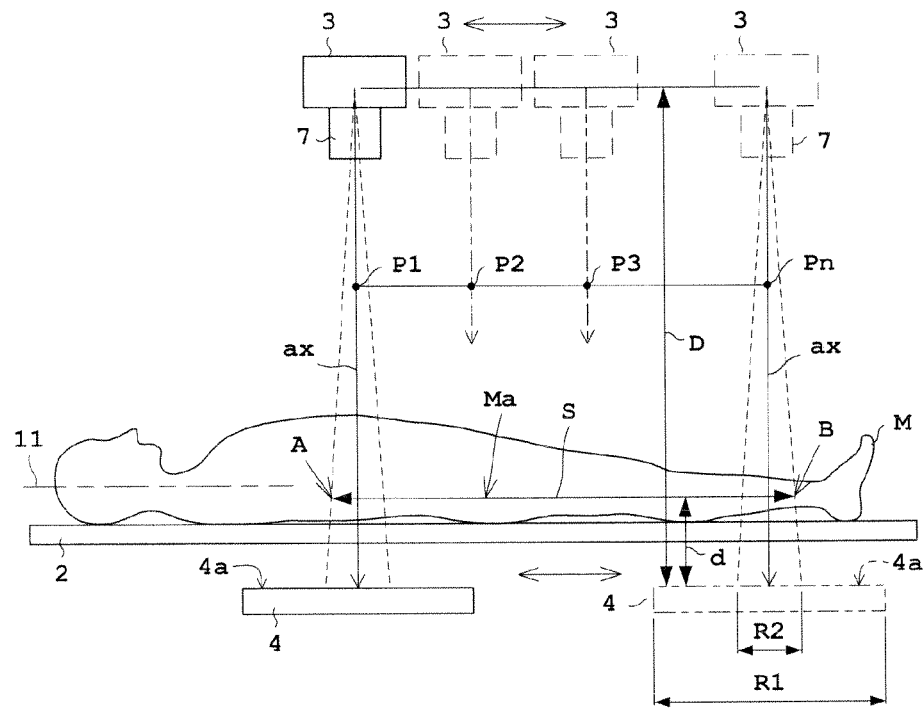
FIG. 2 is a view illustrating a setting method for long-size radiography.
Figure 3:
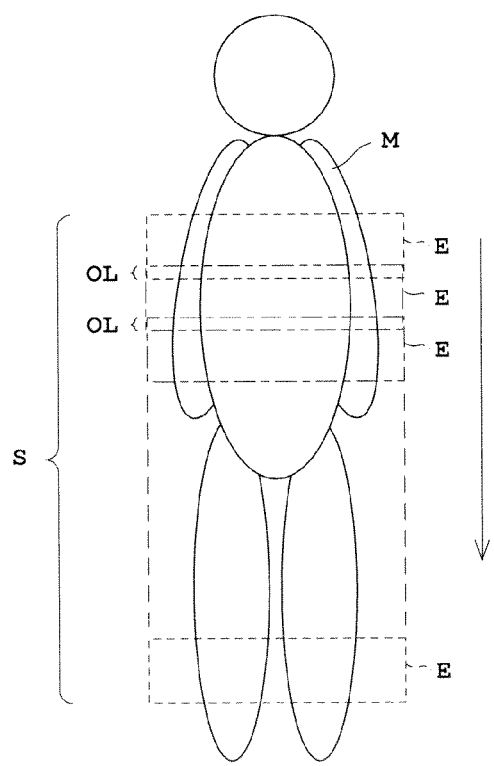

Settings and the like for long-size radiography are made through the input unit 21. FIG. 2 is a view illustrating a setting method for long-size radiography. As shown in FIG. 2, a long-size radiographic range S is set between sign A and signs B. Setting of positions of sign A and sign B is carried out while emitting visible light from a projector such as a collimator lamp or laser marker (not shown) provided for the collimator 7. Further, radiographing positions of the X-ray tube 3, FPD 4 and so on for each separate action of long-size radiography are set by setting a radiographic distance D between the X-ray tube 3 and the detecting plane 4a of FPD 4, and setting a distance d between the detecting plane 4a of FPD 4 and an arbitrary radiographed plane Ma of the inspection object M. FIG. 3 is view illustrating the long-size radiographic range S, radiographic ranges E for separate actions, overlap portions OL and so on. Two adjoining radiographic ranges E have an overlap portion OL set thereto.

Next, a construction for creating a long image will be described. Reference is made back to FIG. 1. The X-ray apparatus 1 further includes an X-ray tube position sensor 31 for acquiring position information on the X-ray tube 3 in the body axis direction 11 of the inspection object M for each separate X-raying action, an X-ray irradiation area discriminator 33 for discriminating X-ray irradiation area images G2 (see FIG. 4 (a)) irradiated with X-rays, by conducting image processing on X-ray images G1 acquired by the FPD 4, and a long image creator 35 for creating a long image G3 by splicing the X-ray irradiation area images G2 together, the X-ray irradiation area images G2 being shifted based on the position information P on the X-ray tube 3 so that the center of each of the X-ray irradiation area images G2 in the direction of movement of FPD 4 coincide with a position of X-ray incidence at the time of radiography. The X-ray tube position sensor 31 corresponds to the position information acquirer in this invention.

The X-ray tube position sensor 31 acquires position information P on the X-ray tube 3 in the body axis direction 11 of the inspection object M for each separate X-raying action. The position information P on the X-ray tube 3 by this X-ray tube position sensor 31 is actual position information P including errors. The X-ray tube position sensor 31 is formed of a linear encoder or the like. In FIG. 2, signs P1, P2 and P3 denote position information P for a first, a second and a third X-raying actions (or positions therefor), respectively, and sign Pn denotes position information P for the n-th. Note that the first, second, third, . . . n-th position information P1, P2, P3, . . . Pn will be indicated by sign P when not particularly be distinguished.

Figure 4:
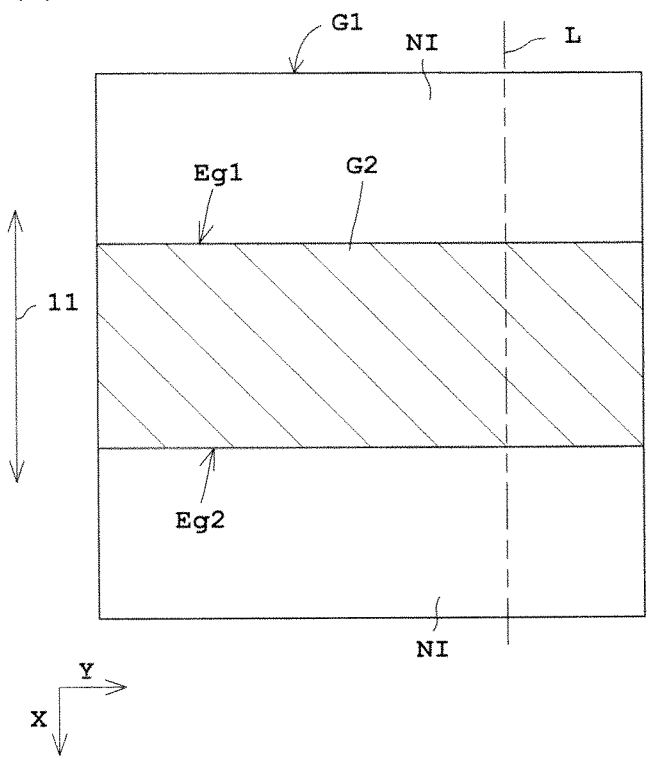
FIG. 4, (a) is a view illustrating operation of an X-ray radiation area discriminator, (b) is a view showing a profile of pixel values on line L in (a), and (c) is a view showing an example of output images of the X-ray radiation area discriminator.
Figure 4:
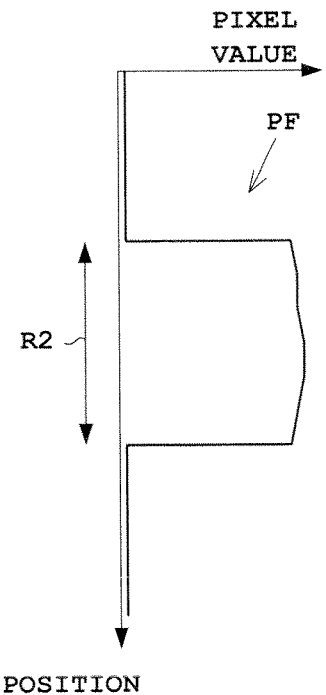
Figure 4:
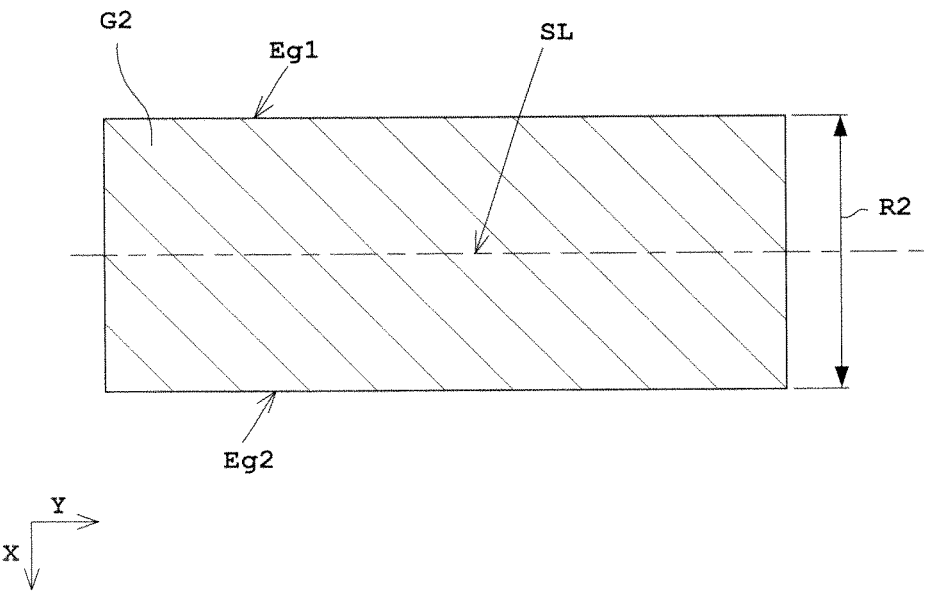

The X-ray radiation area discriminator 33 discriminates, for each separate X-raying action, an X-ray irradiation area image G2 which is an area in the X-ray image G1 reflecting X-rays collimated to a slit shape. Assume that the X-ray image G1 in FIG. 4 (*a*) is, for example, an image obtained by detecting X-rays in the entire detecting area of the FPD 4. The X-ray irradiation area discriminator 33 discriminates an X-ray irradiation area image G2 within this X-ray image G1. In FIG. 4 (*a*), images NI represent areas shielded off by the leaves of the collimator 7.

FIG. 4 (*b*) is a view showing a profile PF of pixel values (luminance) on line L of FIG. 4 (*a*). The X-ray irradiation area image G2 is discriminated, for example, by detecting positions as boundaries where pixel values indicating X-ray intensity change significantly. As a specific process, an existing technique such as edge detection process, for example, is used. Although the X-ray image G1 does not need to be detected in the entire detecting area of the FPD 4, it needs to be a larger image than the X-ray irradiation area image G2 in order to obtain the effect of this invention.

FIG. 4 (*c*) is a view showing an example of output images of the X-ray irradiation area discriminator 33. In this embodiment, as shown in FIG. 4 (*c*), the X-ray irradiation area discriminator 33 clips and extracts the X-ray irradiation area image G2 from the X-ray image G1. That is, the X-ray irradiation area discriminator 33 outputs only the X-ray irradiation area image G2.

The X-ray irradiation area discriminator 33 adds the position information P on the X-ray tube 3 to the X-ray irradiation area image G2 for each separate X-raying action. That is, a correlation is made between the X-ray irradiation area image G2 and the position information P on the X-ray tube 3 at the time the X-ray irradiation area image G2 is acquired, and the position information P on the X-ray tube 3 is included in the X-ray irradiation area image G2, for example. A process for this correlation is carried out for each X-ray irradiation area image G2. Note that although the position information P on the X-ray tube 3 is added to the X-ray irradiation area image G2, the X-ray irradiation area image G2 and the position information P may remain separate.

According to the construction in Embodiment 1, variations in the positional relationship between the X-ray tube 3 and FPD 4 are permitted to some extent in order to simplify control. This may point to the fact that the X-ray tube 3 and FPD 4 do not move in the same behavior. From this line of thought it may seem that displacement will occur when the X-ray irradiation area images G2 are spliced together to acquire a long image G3. However, according to the construction of this invention, such a situation will have no influence on the long image G3.

Figure 5:
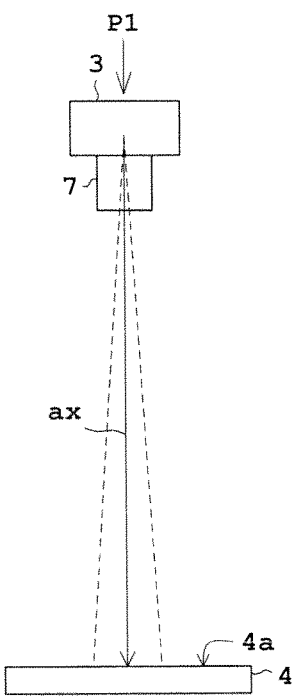
FIG. 5, (a)-(e) are views illustrating an X-ray radiation area image and position information.
Figure 5:
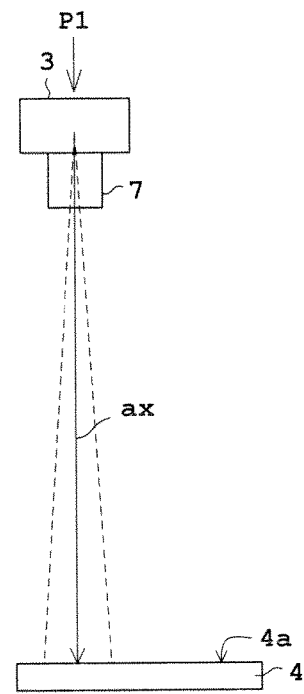
Figure 5:
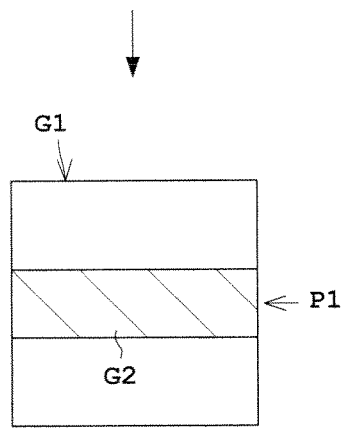
Figure 5:
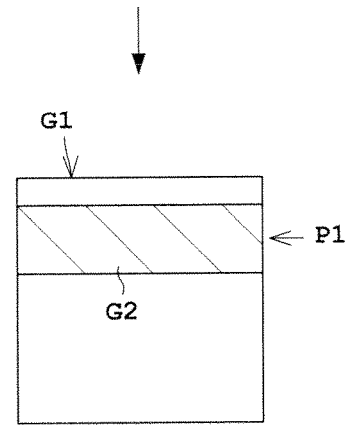
Figure 5:
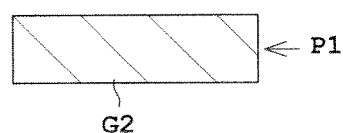

FIG. 5 illustrates the reason therefor. FIG. 5 (*a*) shows a state where irradiating X-rays contracted by the collimator 7 are located centrally of the detecting plane 4*a* of FPD 4. It is, so to speak, a case where the X-ray tube 3 and FPD 4 are moving ideally. On the other hand, FIG. 5 (*b*) shows a state where the FPD 4 is shifted rightward with respect to the FPD 4 of FIG. 5 (*a*), and the irradiating X-rays contracted to the same shape as in FIG. 5 (*a*) are located adjacent an end of the detecting plane 4*a*. It is, so to speak, a case where the X-ray tube 3 and FPD 4 are moving astray from the ideal.

The X-ray tubes 3 of FIGS. 5 (*a*) and 5 (*b*) are both in position P1 corresponding to position information P1. FIGS. 5 (*c*) and 5 (*d*) show X-ray images G1 acquired by X-raying in the states of FIGS. 5 (*a*) and 5 (*b*), respectively. The X-ray irradiation area discriminator 33 discriminates X-ray irradiation area images G2 from the X-ray images G1. FIG. 5 (*e*) shows a discriminated X-ray irradiation area image G2. That is, when radiography is done with the X-ray tube 3 is in the same position P1 as in FIGS. 5 (*a*) and 5 (*b*), since the position P1 for radiography is the same, the X-ray irradiation area images G2 acquired are the same after all wherever on the detecting plane 4*a* of FPD 4 X-rays may irradiate. Then, a spatial relationship between the X-ray irradiation area image G2 and the position shown by the position information on the X-ray tube 3 will not change with displacements of the FPD 4 relative to the X-ray tube 3. Therefore, if a long image is generated while shifting the X-ray irradiation area images G2 based on the correlated position information P, the result will be an image without displacement.

The long image creator 35 creates a long image by shifting each of the X-ray irradiation area images G2, which are fragments of extracted shapes of the X-ray irradiation area, based on the position information P on the X-ray tube 3, and splicing the X-ray irradiation area images G2 together. The long image creator 35 arranges the X-ray irradiation area images G2 in an order of the radiographic ranges E for the separate actions in the long-size radiographic range S of FIG. 3. Specifically, based on the position information P (P1, P2, P3, . . . , Pn) for the separate actions acquired by the X-ray tube position sensor 31, it calculates relative distances between position information P1 used as position reference, and position information P2, P3 . . . , Pn on the X-ray tube 3 for the separate actions. Using the calculated relative distances, it shifts and arranges the X-ray irradiation area images G2 corresponding to the position information P (P1, P2, P3, . . . , Pn). The plurality of X-ray irradiation area images G2 are spliced together in the arranged positions to generate a single long image.

Figure 6:
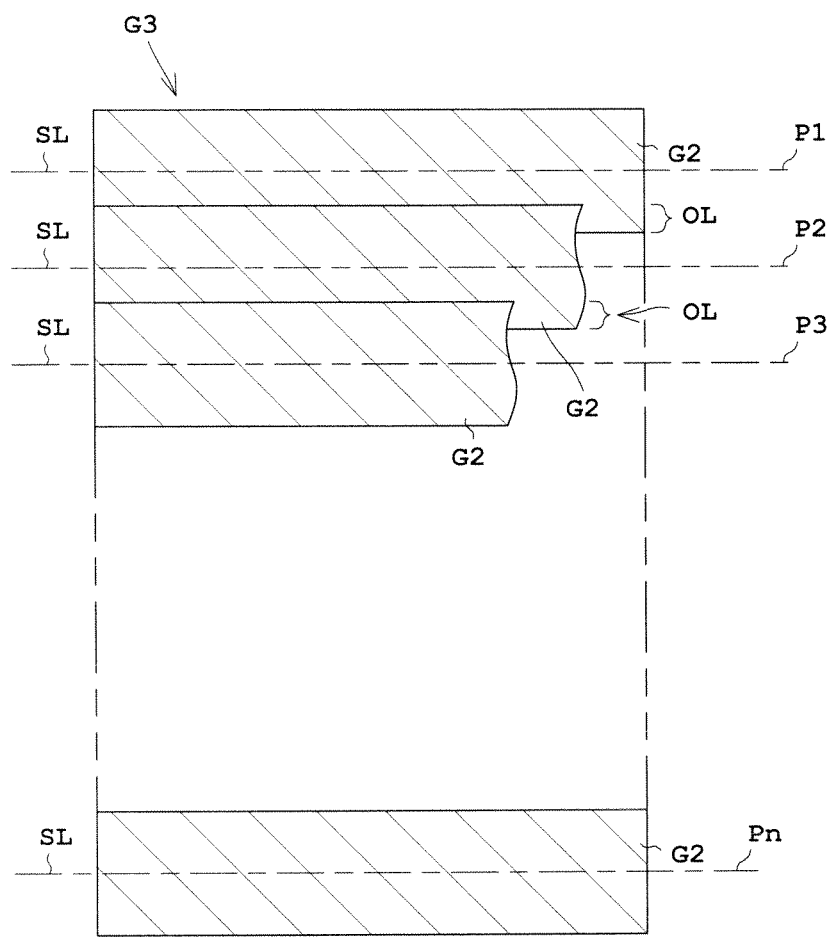
FIG. 6 is a view illustrating operation of a long image creator.

When shifting and arranging the X-ray irradiation area images G2, the relative distances are based on reference lines SL of the respective irradiation area images G2 (see FIG. 6). As shown in FIG. 4 (*c*), for example, the reference lines SL are calculated by the X-ray irradiation area discriminator 33 or the main controller 17 to have a value for halving width R2 of the X-ray irradiation area images G2. If edges Eg1 and Eg2 of a discriminated X-ray irradiation area image are not straight lines, the reference line SL may be obtained by straightening an undulating line after calculating one half of the width R2, or may be obtained by calculating one half of the width R2 after straightening the undulating edges Eg1 and Eg2. The straightening is done using a statistical value (average value, maximum value, minimum value, mode value or median value), for example. For expediency of illustration, FIG. 6 is partly broken away in order to show overlap portions OL of the X-ray irradiation area images G2.

Next, operation of the X-ray apparatus 1 will be described. First, long-size radiographic conditions are set. The long-size radiographic conditions set include, for example, the long-size radiographic range S, radiographic ranges E for the separate actions, overlap portions OL, the number of times of radiographing actions, and so on. This setting is carried out through the input unit 21, for example.

A radiographing position for each separate action is set as follows, for example. Of the detecting plane 4*a* of FPD 4 irradiated with X-rays formed into the shape of a slit, the area R2 in the direction of movement of FPD 4 is set to 100 mm, and the overlap portion OL where two adjoining X-ray irradiation areas overlap is set to 10 mm. In this case, the relative moving distance of the X-ray tube 3 is 100 mm–10 mm=90 mm. That is, the X-ray tube 3 takes an X-raying action at every 90 mm movement. Therefore, assuming that the radiographing position for the first image is 0 mm as reference, the radiographing position for the second image will be 90 mm and the radiographing position for the third image will be 180 mm.

An X-ray radiography is conducted. In accordance with the long-size radiographic conditions, the main controller 17 carries out movement control and the like of the X-ray tube mover 8 and X-ray detector mover 9. The X-ray tube 3 and FPD 4 make parallel translation independently, and the X-ray tube 3 emits X-rays a plurality of times, i.e. in separate radiographing positions. The X-rays emitted from the X-ray tube 3 pass through the inspection object M, and fall on the detecting plane 4a of FPD 4. The FPD 4 detects the incident X-rays and outputs X-ray images G1. The outputted X-ray images (X-ray detection signals) G1 are digitized by the analog-to-digital converter 13. The digitized X-ray images are stored in the storage unit 23 and the like after required processes are carried out by the image processor 15.

Whenever X-raying is carried out in each radiographing position, the X-ray tube position sensor 31 acquires (detects) actual position information P on the X-ray tube 3 which is coordinates information in the direction of movement of the X-ray tube 3 (detect), and transfers it to the X-ray irradiation area discriminator 33 or storage unit 23.

The X-ray images G1 stored in the storage unit 23 and the like are transferred to the X-ray irradiation area discriminator 33. The X-ray irradiation area discriminator 33 discriminates from among the X-ray images G1 the areas irradiated with X-rays contracted to the shape of a slit. And in this embodiment, the X-ray irradiation area discriminator 33 outputs and stores in the storage unit 23 the X-ray irradiation area images G2 formed of the discriminated X-ray irradiation areas clipped and extracted. At this time, the X-ray irradiation area discriminator 33 adds the position information P on the X-ray tube 3 of the time of X-raying acquired by the X-ray tube position sensor 31 to the X-ray irradiation area images G2 corresponding to this position information P. The addition of the position information P to the X-ray irradiation area images G2 is not limited to the X-ray irradiation area discriminator 33 but, for example, the main controller 17 may do this to the X-ray irradiation area images G2 stored in the storage unit 23.

All X-raying for the long-size radiographic range S is completed. The long image creator 35 creates a long image G3 by shifting and superimposing the X-ray irradiation area images G2 relative to one another, based on the X-ray irradiation area images G2 stored in the storage unit 23 and the position information P on the X-ray tube 3 added to the X-ray irradiation area images G2 (see FIG. 6). The created long image G3 is displayed on the display unit 19 and/or stored in the storage unit 23.

According to this embodiment, the X-ray tube 3 emits X-rays toward the inspection object M, and is moved by the X-ray tube mover 8 along the body axis direction 11 of the inspection object M. The FPD 4 is provided opposite the X-ray tube 3 for detecting X-rays transmitted through the inspection object M and outputting them as X-ray images G1. The X-ray detector mover 9 moves the FPD 4 along the body axis direction 11 of the inspection object M independently of the X-ray tube 3. A collimator 7 is provided on the X-ray emitting side of the X-ray tube 3. The collimator 7, while contracting emitted X-rays to the areas R2 narrower than the detecting area R1 of FPD 4 in the direction of movement of FPD 4, is movable to accompany the X-ray tube 3. The X-ray irradiation area discriminator 33 discriminates, for separate X-raying actions, X-ray irradiation area images G2 which are areas in the X-ray images G1 having received collimated X-rays. The X-ray tube position sensor 31 acquires position information P on the X-ray tube 3 for each separate X-raying action. And the long image creator 35 creates a long image G3 by shifting the X-ray irradiation area images G2, based on the position information P, so that the center of each of the X-ray irradiation area images G2 in the direction of movement of FPD 4 coincide with a position of X-ray incidence at the time of radiography, and by splicing the X-ray irradiation area images G2 together.

That is, in the long-size radiography with the FPD 4 moving independently of the X-ray tube 3, the X-ray irradiation area discriminator 33 discriminates, for separate X-raying actions, X-ray irradiation area images G2 which are areas in the X-ray image G1 having received the collimated X-rays. The X-ray tube position sensor 31 acquires position information P on the X-ray tube 3 for the separate X-raying actions. And the long image creator 35 creates a long image by shifting the X-ray irradiation area images G2, based on the position information P, so that the center of each of the X-ray irradiation area images G2 in the direction of movement of FPD 4 coincide with a position of X-ray incidence at the time of radiography, and by splicing the X-ray irradiation area images G2 together. Consequently, even when the relative position between the X-ray tube 3 and FPD 4 is variable instead of being constant, the X-ray irradiation area images G2 can be obtained reliably, and the X-ray irradiation area images G2 can be spliced to one another with high accuracy. Further, there is no need to uniform starting timing and moving speed of the X-ray tube 3 and FPD 4, which can simplify control and make the apparatus inexpensive.

For example, the motor of the X-ray detector mover 9 for moving the FPD 4, instead of an expensive XC servomotor, may be a relatively inexpensive motor such as a DC brush motor. There is no need to uniform starting timing and moving speed of the X-ray tube 3 and FPD 4. Therefore, an operation command conventionally given to the X-ray tube mover 8 and X-ray detector mover 9 at the same time can be given only to the X-ray tube mover 8. To the X-ray detector mover 9, for example, an operation command can be given after the first X-raying action.

Figure 7:
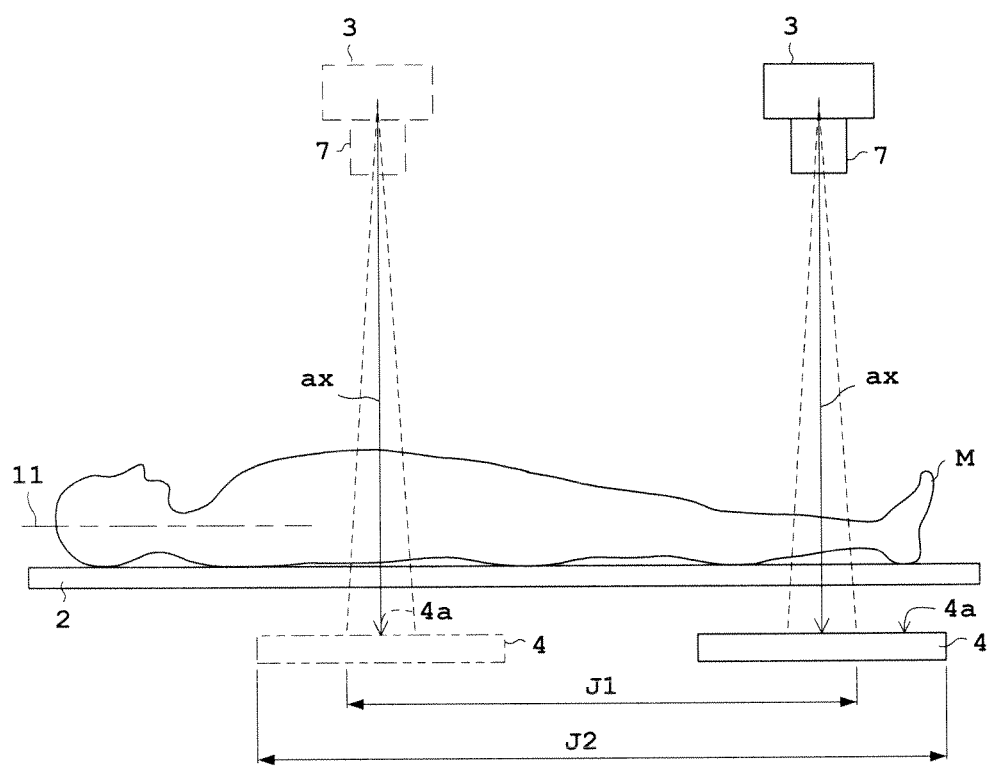
FIG. 7 is a view illustrating an advantage.

A conventional X-ray apparatus is controlled such that an X-ray axis ax of X-rays emitted from the X-ray tube 3 is located at the center of the detecting plane 4a which is the X-ray detecting area of FPD 4. Therefore, the long-size radiographic range S was, as shown in FIG. 7, distance J1 corresponding to the moving distance of FPD 4. However, since this invention allows X-raying to be done in any position on the detecting plane 4a of FPD 4, even if the moving distance of FPD 4 is the same as in the prior art, the long-size radiographic range S can be set wide like distance J2 in FIG. 7.

The X-ray tube position sensor 31 is used to acquire position information P on the X-ray tube 3. Since actual position information P on the X-ray tube 3 can be acquired by this, even when errors occur, the X-ray irradiation area images G2 can be spliced together with high accuracy.

The X-ray irradiation area images G2 are images extracted from the X-ray images G1. Images other than the X-ray irradiation area images G2 can be removed, which can make a data volume smaller than the original X-ray images G1.

The X-ray irradiation area discriminator 33 adds position information P to the X-ray irradiation area image G2 for each separate X-raying action. This can simplify control of the X-ray irradiation area images G2 and position information P. For example, even when a change occurs to the order of the plurality of X-ray irradiation area images G2 for creating a long image G3, the positions of the X-ray irradiation area images G2 at the time of splicing can be known from the position information P added to the X-ray irradiation area images G2.

The X-ray tube mover 8 moves the X-ray tube 3 at a constant speed. This simplifies control and assures long images G3 of stable quality.

An advantage over Patent Document 3 will be described here. According to this embodiment, the X-ray irradiation area images G2 corresponding to slit-shaped images are discriminated from the X-ray images G1. The X-ray irradiation area images G2 are areas of irradiating X-rays contracted to the area R2 narrower than the detecting area R1 of the FPD 4. Therefore, when X-rays are emitted from the X-ray tube 3 in a predetermined position, even if the FPD 4 is displaced to a certain extent, the X-ray irradiation area image G2 discriminated and obtained is the same as long as the irradiation X-rays are within the detecting area R1 of the FPD 4. Further, if the position information P on the X-ray tube 3 used is based on actual positions, the X-ray irradiation area images G2 can be spliced together in a way to allow for displacement of the X-ray tube 3. Therefore, the X-ray irradiation area images G2 discriminated from the X-ray images G1 may be shifted based on the acquired position information P on the X-ray tube 3, and then the X-ray irradiation area images G2 may be spliced to one another. In this way, a long image G3 with the influence of displacement suppressed can be obtained regardless of the relative moving distance of the X-ray tube 3 and FPD 4.

Embodiment 2

Figure 8:
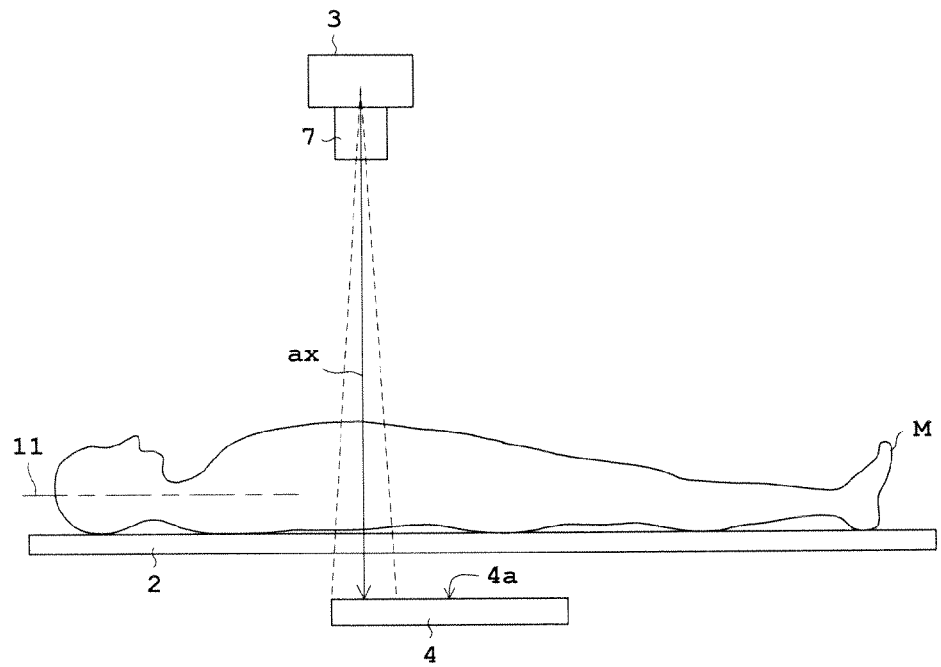
FIG. 8, (a) and (b) are views illustrating operation of an X-ray apparatus according to Embodiment 2.
Figure 8:
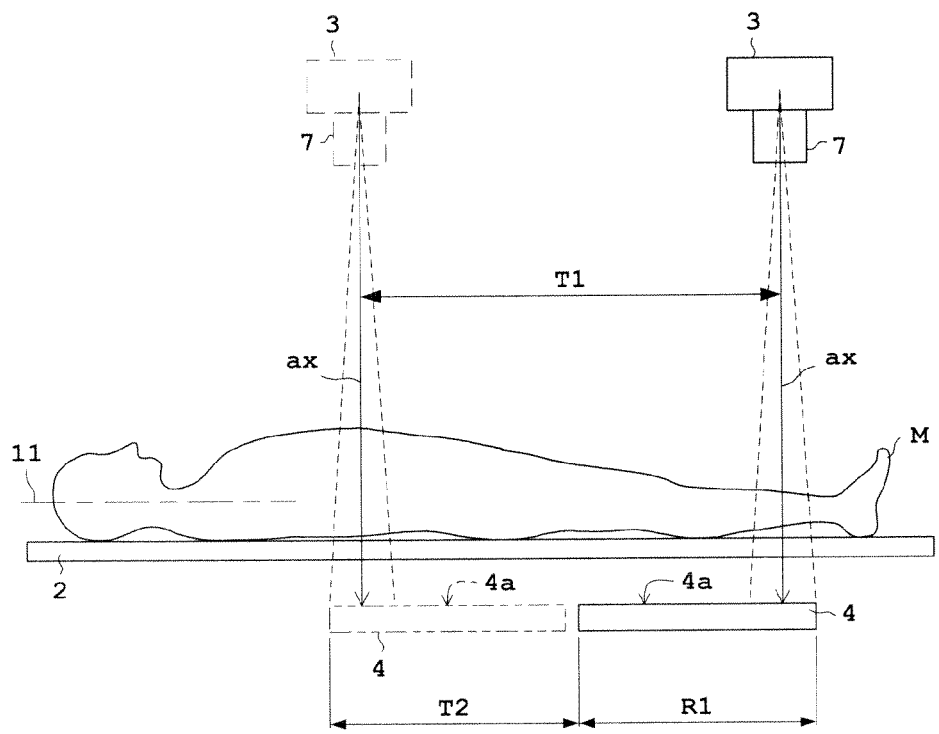

Next, Embodiment 2 of this invention will be described with reference to the drawings. FIG. 8 (*a*) and FIG. 8 (*b*) are views illustrating operation of an X-ray apparatus according to Embodiment 2. Description of constructions overlapping those of Embodiment 1 will be omitted.

In Embodiment 1 described above, a method of moving the FPD 4 is not specified particularly concerning the FPD4 moving independently of the X-ray tube 3. So, in Embodiment 2, the X-ray detector mover 9 moves the FPD 4 slower than the X-ray tube 3, for example.

The X-ray detector mover 9 moves the FPD 4 on average slower than the X-ray tube 3. The phrase on average slower does not mean that the moving speed of FPD 4 momentarily becomes slower than the X-ray tube 3, but means that an average speed is slow over the moving distance of the X-ray tube 3 and FPD 4 moving from start to finish of long-size radiography. Making it move slow on average can be carried out by the following operation. As shown in FIG. 8 (*a*), for example, at the start of radiography, the X-ray irradiation area including X-ray axis ax is located in an area adjacent one end of the detecting plane 4*a* of FPD 4, which end is backward in the direction of movement of the detecting plane 4*a*. And as shown in FIG. 8 (*b*), at the finish of radiography, the X-ray irradiation area is located in an area adjacent the other end of the detecting plane 4*a* of FPD 4, which end is forward in the direction of movement of the detecting plane 4*a*.

According to Embodiment 1, as long as X-rays fall within the detecting plane 4*a* of FPD 4, X-raying may be carried out in any position on the detecting plane 4*a*. While the X-ray tube 3, as it emits X-rays, moves a distance set beforehand, the FPD 4 is moved a moving distance set beforehand. That is, by using the detecting plane 4*a* of FPD 4 effectively, an amount of movement of the FPD 4 can be restrained. Assume, for example, a relationship (T1=R1+T2) where moving distance T1 of the X-ray tube 3 in X-raying is equal to a sum of size R1 of the detecting plane 4*a* of FPD 4 and moving distance T2 of FPD 4. In this case, the amount of movement of FPD 4 can be minimized. For expediency of description, however, the width R2 of the X-ray irradiation area which is a spread of X-rays is not taken into account.

According to this embodiment, the X-ray detector mover 9 moves the FPD 4 slower on average than the X-ray tube 3. Conventionally, a high-output motor is used in order to move the FPD 4 which is heavier than the X-ray tube 3 similarly to the X-ray tube. However, by moving the FPD 4 slower than the X-ray tube 3, it is possible to use a motor having a lower output than in the prior art. Therefore, a power-saving and inexpensive motor can be used, thereby making the X-ray apparatus 1 inexpensive.

Embodiment 3

Next, Embodiment 3 of this invention will be described with reference to the drawings. Description of constructions overlapping each embodiment will be omitted.

In each embodiment described above, the X-ray tube position sensor 31 acquires position information P on the X-ray tube 3 for each separate X-raying action, and the acquired position information P is added to the X-ray irradiation area images G2 extracted by the X-raying. However, when X-raying time intervals are constant and the moving speed of the X-ray tube 3 is constant, for example, it is not necessary to provide the X-ray tube position sensor 31 to actually measure the position information P on the X-ray tube 3.

That is, the main controller 17, before X-raying or after X-raying, notifies X-raying time interval information U and X-ray tube moving speed information V to the long image creator 35. The long image creator 35 calculates a radiographing position P (=U×V×N) for each separate action from the X-raying time interval information U, X-ray tube moving speed information V and number of times N of radiography. That is, if the time intervals of X-raying and the moving speed of the X-ray tube 3 are known beforehand, radiographing position P of the X-ray tube 3 for each separate X-raying action can be determined. Based on the position information P on the X-ray tube 3 which is information on position P for each radiographic action, the long image creator 35 creates a long image G3. Note that the main controller 17 may calculate position information P on the X-ray tube 3 which is information on radiographing position P for each separate action from the X-raying time interval information U and X-ray tube moving speed information V, and notify it to the long image creator 35. The X-ray tube moving speed information V corresponds to the X-ray source moving speed information in this invention.

According to this embodiment, position information P is calculated from radiographing time interval information U and X-ray tube moving speed information V. When the X-raying time interval information U and the moving speed of the X-ray tube 3 are constant, it becomes unnecessary to provide the X-ray tube position sensor 31, for example. This can simplify the construction, thereby making the apparatus inexpensive.

This invention is not limited to the foregoing embodiments, but may be modified as follows:

(1) In each embodiment described above, as shown in FIG. 1, the inspection object M is placed on the top board 2, and a plurality of X-ray images G1 for long-size radiography are obtained by the X-ray tube 3 and FPD 4 arranged opposite each other above and below the top board 2. However, a screen (also called a stand) may be used instead of the top board 2. Long-size radiography is conducted by placing the inspection object M in a standing position along the screen, and with the X-ray tube 3 and FPD 4 arranged opposite each other forward and rearward (laterally) of the screen.

(2) In each embodiment and modification (1) described above, at least one of the X-ray tube 3 and FPD 4 need not move at a constant speed. For example, the FPD 4 may be accelerated or decelerated in movement. The FPD 4 may make a movement combining at least two of constant-speed movement, acceleration and deceleration.

(3) In each embodiment and each modification described above, as shown in FIG. 4 (c), the X-ray irradiation area discriminator 33 clips and extracts the X-ray irradiation area image G2 from the X-ray image G1. However, for example, the X-ray irradiation area discriminator unit 33 may discriminate the X-ray irradiation area images G2, and instead of clipping off the images NI of the areas not irradiated with X-rays, may output an X-ray image with the images NI labeled "no information". The images NI may be outputted as they are, and may be outputted after reducing noise joining the images NI as they are.

(4) In each embodiment and each modification described above, the X-ray irradiation area discriminator 33 is provided separately from the image processor 15. However, the image processor 15 may include the X-ray irradiation area discriminator 33.

(5) In each embodiment and each modification described above, each X-raying action for the long-size radiography is taken while the X-ray tube 3 and FPD 4 are making parallel translation relative to the body axis direction 11 of the inspection object M, to acquire the X-ray irradiation area images G2 and the position information P on the X-ray tube 3. However, X-rays may be emitted while changing the direction of the X-ray tube 3. That is, the X-ray tube 3 oscillates about an axis (e.g. horizontal axis) set beforehand to follow the body axis direction 11 of the inspection object M.

Figure 9:
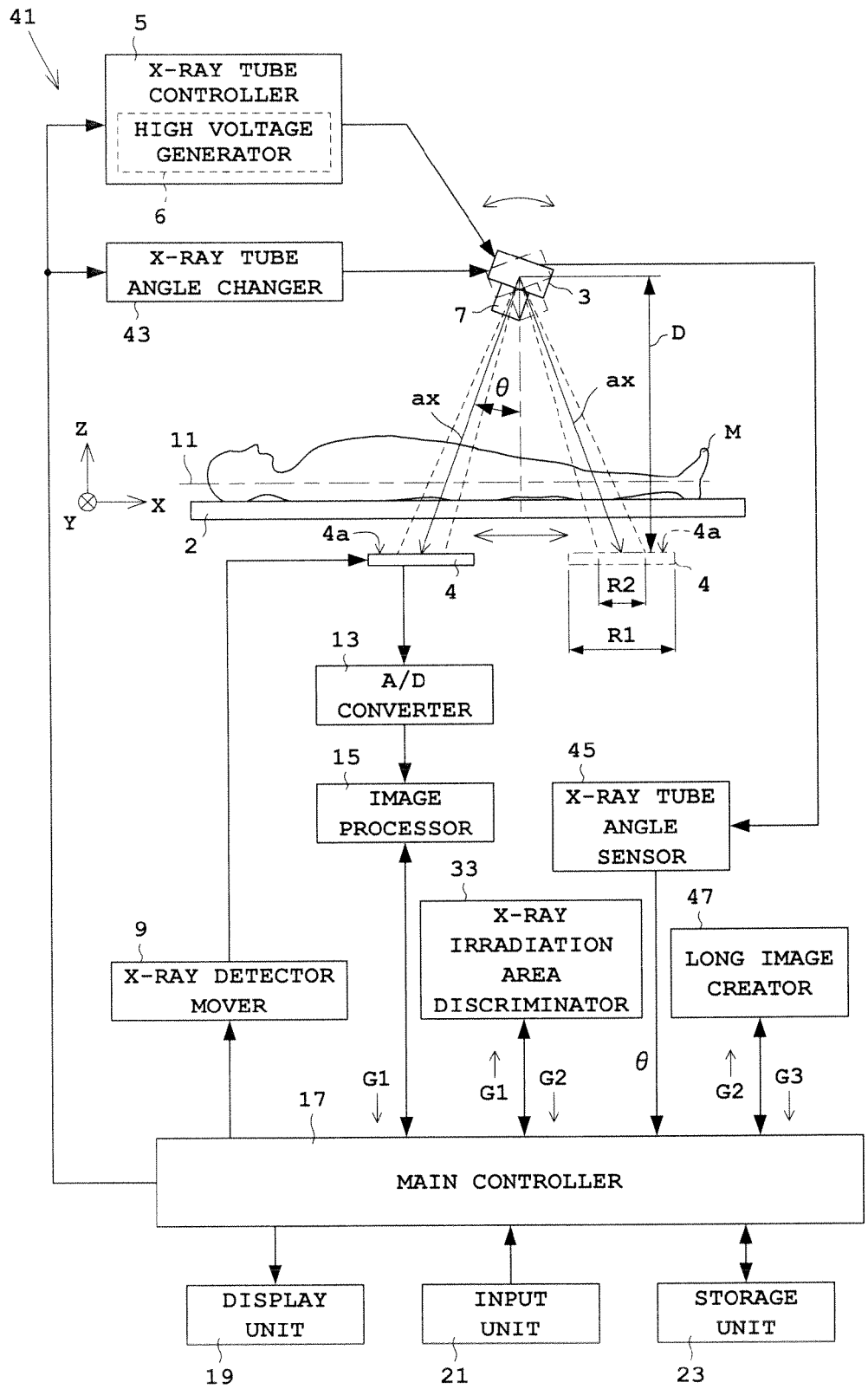
FIG. 9 is a view showing an outline construction of an X-ray apparatus according to a modification.

Reference is made to FIG. 9. An X-ray apparatus 41, first compared with the X-ray apparatus 1 of FIG. 1, includes an X-ray tube angle changer 43 in place of the X-ray tube mover 8, and an X-ray tube angle sensor 45 in place of the X-ray tube position sensor 31. The X-ray tube angle changer 43 changes the angle of the X-ray tube 3 about an axis set beforehand to follow the body axis direction 11 of the inspection object M. The X-ray tube angle sensor 45 acquires angle information θ on the X-ray tube 3 for each separate X-raying action. And in this modification, a long image creator 35 creates a long image G3 by splicing X-ray irradiation area images G2 together, the X-ray irradiation area images G2 being shifted based on the angle information θ, so that the center of each of the X-ray irradiation area images G2 in the direction of movement of FPD 4 coincide with a position of X-ray irradiation at the time of radiography.

Figure 10:
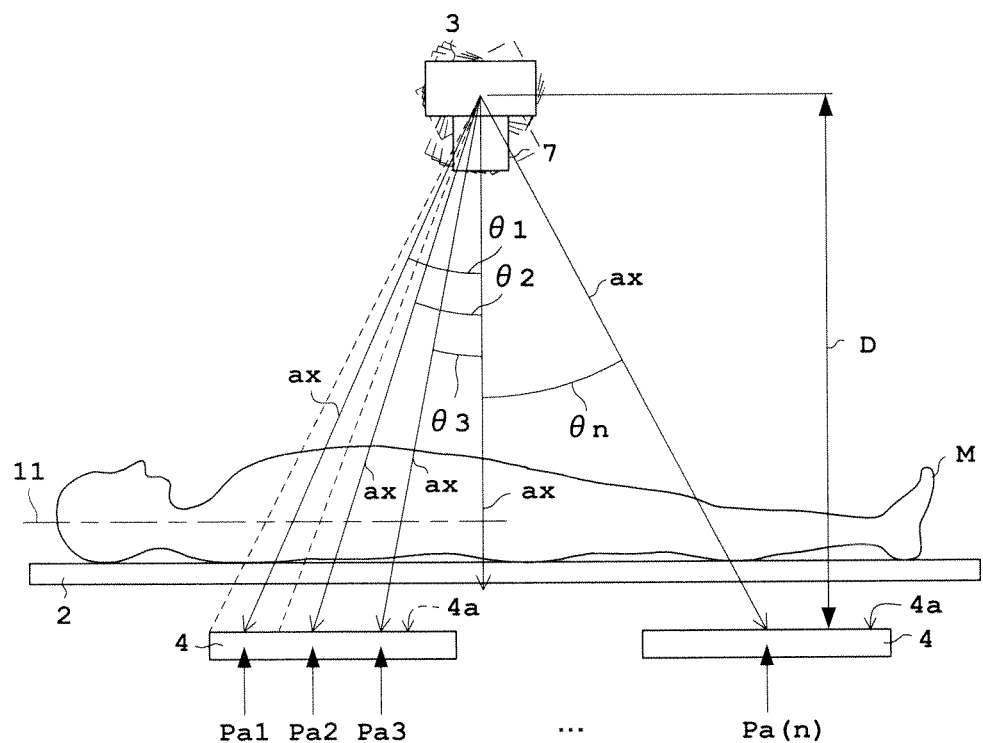
FIG. 10 is a view illustrating a method of calculating positions for X-ray emission.

A method of calculating positions to which the X-ray irradiation area images G2 are shifted based on the angle information θ will be described with reference to FIG. 10. First, a reference is set to an angle of the X-ray tube 3 when X-rays are emitted from the X-ray tube 3 to have the central axis ax of the X-rays extending in a direction (Z-direction) perpendicular to the body axis direction 11 of the inspection object M. Angles based on the angle of the X-ray tube 3 at the above time constitute angle information θ. A radiographic distance D between the focus of X-ray tube 3 and the detecting plane 4a of FPD 4 is set. Positions Pa (=D×tan θ) of X-ray irradiation are calculated from the angle information θ and radiographic distance D. Positions Pa (Pa1, Pa2, Pa3, . . . , Pa (n)) of X-ray irradiation are calculated from angle information θ (θ1, θ2, θ3, . . . , θn) for separate X-raying actions. The angle information θ on the X-ray tube 3 may be added to the X-ray irradiation area image G2 for the separate X-raying actions. Positions Pa of X-ray irradiation are calculated by the long image creator 47, but they may be calculated by the main controller 17 and transferred to the long image creator 47.

The X-ray tube angle changer 43 corresponds to the X-ray source angle changer in this invention. The X-ray tube angle sensor 45 corresponds to the angle information acquirer in this invention.

The X-ray apparatus 41 may have the following construction. The X-ray detector mover 9 may move the FPD 4 slower on average than moving speed of the X-ray axis ax emitted from the X-ray tube 3. The angle information θ on the X-ray tube 3, instead of being the angle information θ acquired by the X-ray tube angle sensor 45, may be calculated from the X-raying time interval information U and an angular speed of the X-ray tube 3. That is, when the X-raying time intervals are constant and the moving speed of X-ray axis ax emitted from the X-ray tube 3 is constant, these enable the position Pa of X-ray irradiation in each separate action to be calculated to determine an extent of shifting of the X-ray irradiation area image G2 acquired from each X-raying action. Note that the moving speed of X-ray axis ax emitted from the X-ray tube 3 need not be constant.

This modification, although different from Embodiment 1 in that long-size radiography is carried out while changing the direction of the X-ray tube 3, provides the same effects as Embodiment 1.

(6) Each embodiment and each modification have been described using the FPD 4 as an example of X-ray detector. However, an image intensifier and a camera may be used.

(7) In each embodiment and each modification described above, as shown in FIG. 3, the radiographic range E of each separate action in the long-size radiography is slit-shaped in order to carry out slot radiography. This may, for example, be a rectangular radiographic range other than the shape of a slit.

REFERENCE SIGNS LIST 1, 41 . . . X-ray apparatus
3 . . . X-ray tube
4 . . . flat panel X-ray detector (FPD)
4a . . . detecting plane
7 . . . collimator
8 . . . X-ray tube mover
9 . . . X-ray detector mover
11 . . . body axis direction
17 . . . main controller
31 . . . X-ray tube position sensor 33 ... X-ray irradiation area discriminator
35, 47 ... long image creator
43 ... X-ray tube angle changer
45 ... X-ray tube angle sensor
M ... inspection object
R1 ... detecting area
R2 ... narrow area
G1 ... X-ray images
G2 ... X-ray irradiation area images
G3 ... long image
P (P1, P2, P3, ..., Pn) ... position information (positions)
SL ... reference line

The invention claimed is:

1. An X-ray apparatus comprising:
an X-ray source for emitting X-rays toward an inspection object;
an X-ray source mover for moving the X-ray source along a body axis of the inspection object;
an X-ray detector disposed opposite the X-ray source for detecting X-rays transmitted through the inspection object and outputting them as X-ray images;
an X-ray detector mover for moving the X-ray detector along the body axis of the inspection object independently of the X-ray source;
a collimator disposed on an X-ray emitting side of the X-ray source to be movable with the X-ray source for contracting emitted X-rays;
an X-ray irradiation area discriminator for discriminating, for separate X-raying actions, X-ray irradiation area images which are areas of the X-ray images where X-rays collimated to an area narrower than a detecting area of the X-ray detector in a direction of movement of the X-ray detector are received;
a position information acquirer for acquiring position information on the X-ray source for the separate X-raying actions; and
a long image creator for creating a long image by shifting the X-ray irradiation area images based on the position information on the X-ray source acquired by the position information acquirer and regardless of a relative moving distance of the X-ray detector, so that a center of each of the X-ray irradiation area images in the direction of movement of the X-ray detector coincide with a position of X-ray incidence at a time of radiography, and by splicing the X-ray irradiation area images together.

2. The X-ray apparatus according to claim 1, wherein the position information acquirer comprises an X-ray source position sensor.

3. The X-ray apparatus according to claim 1, wherein the long image creator calculates the position information from radiographing time interval information and X-ray source moving speed information.

4. The X-ray apparatus according to claim 1, wherein the X-ray irradiation area images are images extracted from the X-ray images.

5. The X-ray apparatus according to claim 1, wherein the X-ray irradiation area discriminator is arranged to add the position information to the X-ray irradiation area images for the separate X-raying actions.

6. The X-ray apparatus according to claim 1, wherein the X-ray source mover is arranged to move the X-ray source at a constant speed.

* * * * *